United States Patent [19]

Kocal

[11] Patent Number: 4,891,466
[45] Date of Patent: * Jan. 2, 1990

[54] HF ALKYLATION PROCESS

[75] Inventor: Joseph A. Kocal, Gurnee, Ill.

[73] Assignee: UOP, Des Plaines, Ill.

[*] Notice: The portion of the term of this patent subsequent to Nov. 8, 2005 has been disclaimed.

[21] Appl. No.: 237,815

[22] Filed: Aug. 29, 1988

Related U.S. Application Data

[63] Continuation-in-part of Ser. No. 123,828, Nov. 23, 1987, Pat. No. 4,783,567.

[51] Int. Cl.$^4$ ............................ C07C 2/68; C07C 2/58
[52] U.S. Cl. ...................................... 585/464; 585/723; 585/724; 585/725
[58] Field of Search ................ 585/723, 724, 725, 464

[56] References Cited

U.S. PATENT DOCUMENTS

| | | | |
|---|---|---|---|
| 3,364,280 | 1/1968 | Kramer | 585/725 |
| 3,870,765 | 3/1975 | McCoy et al. | 260/683.51 |
| 4,180,691 | 12/1979 | Illingworth | 585/455 |
| 4,396,556 | 8/1983 | Kem | 260/970 |
| 4,684,459 | 8/1987 | Klimpel et al. | 209/166 |
| 4,783,567 | 11/1988 | Kocal | 585/723 |

Primary Examiner—Curtis R. Davis
Attorney, Agent, or Firm—Thomas K. McBride; John F. Spears, Jr.

[57] ABSTRACT

A novel liquid acid catalyzed alkylation process utilizing a liquid acid catalyst comprising a surfactant and a liquid acid is disclosed which incorporates a fixed bed of contact material to improve the alkylation reaction zone efficiency. The fixed bed of contact material also allows the process to be efficiently operated at lower acid to olefin mole/mole feed ratios than normally used.

17 Claims, 1 Drawing Sheet

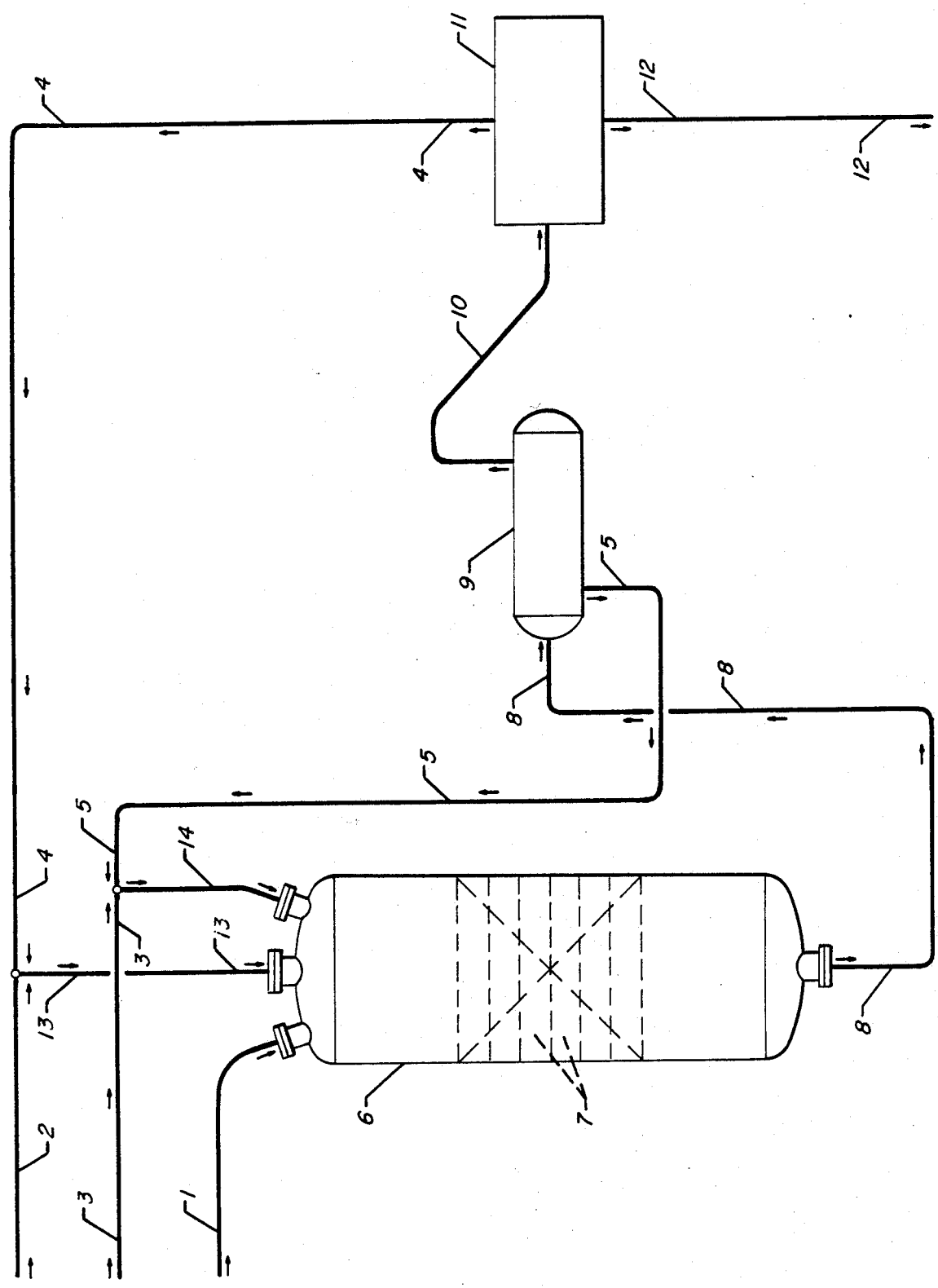

HF ALKYLATION PROCESS

CROSS-REFERENCE TO RELATED APPLICATION

This application is a continuation-in-part of prior copending application Ser. No. 123,828 filed Nov. 23, 1987, now U.S. Pat. No. 4,783,567, the contents of which are incorporated herein by reference thereto.

BACKGROUND OF THE INVENTION

This invention relates to an improved process for the alkylation of a hydrocarbon substrate with an olefin alkylating agent in the presence of a liquid alkylation catalyst. The process utilizes a fixed bed of contact material in the alkylation reaction zone to improve the process efficiency. The process efficiency improvement allows the process to be operated at lower acid to olefin feed ratios with a resulting decrease in the volume of dangerous acid required for processing.

The alkylation of a hydrocarbon substrate with an olefin alkylating agent in the presence of a liquid acid catalyst is a well known method of producing high octane gasoline boiling range products, linear alkylbenzene compounds, and alkylaromatics, among other useful products. A continuing goal in the art is to provide an economically attractive and intrinsically safe acid-catalyzed alkylation process.

The acid utilized in alkylation typically poses great environmental and health risks. Any reduction in required process volumes, storage volumes, etc. is highly desired.

OBJECTS AND EMBODIMENTS

It is therefore an object of the present invention to provide an improved process for the liquid acid-catalyzed alkylation of a hydrocarbon substrate with an olefin acting agent. The acid alkylation process of the instant invention is able to efficiently produce an alkylation product utilizing much less acid catalyst in the feed than conventional acid alkylation processes. Or conversely, the catalyst and process of this invention is able to improve the octane quality of an alkylate in comparison to similar processes of the prior art.

Accordingly, the present invention is a process for the liquid phase alkylation of an olefin acting agent with a hydrocarbon substrate in the presence of a liquid acid alkylation catalyst comprising a surfactant and a liquid acid. The process comprises the steps of admixing a reaction mixture comprising the olefin acting agent, the hydrocarbon substrate, and the liquid acid alkylation catalyst in an alkylation reaction zone operating at alkylation reaction conditions. The alkylation reaction zone is characterized in that it contains a fixed bed of particulate contact material which occupies a portion to all of the volume of the reaction zone. The reaction mixture is passed through the fixed bed of particulate contact material and into a separator. In the separator, the liquid acid alkylation catalyst is separated from the product hydrocarbons. The product hydrocarbons are withdrawn from the separator and further processed to separate and recover the product hydrocarbons. The liquid acid alkylation catalyst recovered from the separator is recycled back to the alkylation reaction zone.

This as well as other objects and embodiments will become apparent upon review of the following, more detailed description of the prior art and the invention.

INFORMATION DISCLOSURE

The use of a fixed bed of contact material in an alkylation process catalyzed with liquid acid is heretofore unknown. The use of solid supported catalysts for hydrocarbon alkylation has been disclosed. U.S. Pat. No. 3,678,120 discloses a catalytic composite comprised of an inert solid support combined with either antimony pentafluoride, hydrogen fluoride, fluosulfonic acid, or mixtures thereof. The '120 patent also discloses the use of the catalyst in a fixed bed catalytic process for the alkylation or isomerization of hydrocarbons.

Many other hydrocarbon alkylation processes employing a fixed bed of a solid catalytic composite are known. For instance, U.S. Pat. No. 4,116,880 discloses an alkylation process and catalyst. The catalyst is comprised of fluorinated graphite along with a Lewis acid selected from the halides of the elements of Group II-A, III-A, IV-B, V, or VI-B of the Periodic Table. U.S. Pat. No. 4,083,885 discloses a process for the alkylation of a hydrocarbon using a fixed bed of catalyst. The fixed bed of catalyst is comprised of graphite intercalated with from 5 to 50 wt.% of a Lewis acid fluoride. Other alkylation processes employing fixed beds of solid supported alkylation catalysts are disclosed in U.S. Pat. Nos. 3,852,371 and 3,979,476.

U.S. Pat. No. 3,839,487 discloses a process for alkylating a paraffin with an olefin. The process is accomplished by introducing the hydrocarbon and liquid acid catalyst at separate points on a plurality of linear fibers in a reaction zone. This patent describes a process performing a function in a similar manner as that of the instant process. However, the '487 patent does not in any manner describe the process of the instant invention or the benefits of the process of the instant invention, namely that a mixture of alkylatable hydrocarbons can be efficiently alkylated with a small amount of liquid acid catalyst by performing the process in a reaction zone containing a fixed bed of inert particulate contact material.

A number of references disclose the use of fixed beds of contact material in an acid catalyzed alkylation process. Among these are U.S. Pat. Nos. 3,155,742 and 3,253,053. Both the '742 and the '053 patents disclose the use of an inert material in an alkylation reaction zone. However, neither of the patents disclose that an activated carbon is usefuul in such a process. Further, in the process of the '053 disclosure, the inert material is not contained in a fixed bed, but is circulated as a viscous material. The process of this invention relates to a liquid phase alkylation process operated in the presence of a fixed bed of activated carbon, thus distinguishing the instant process from the prior art.

U.S. Pat. No. 3,113,981 and French Patent 1,320,122 both disclose the alkylation of hydrocarbons in the presence of a fixed bed of contact material. But unlike the instant process which occurs in the liquid phase, the '981 patent, like the French '122 patent, discloses an alkylation process performed in the vapor phase in the presence of an activated carbon. Additionally, the '981 patent, in claiming an aromatic alkylation process, succinctly states that the results of the vapor phase process are entirely different than those of the liquid phase reaction and implies there is no advantage to using activated carbon in a liquid phase process.

Finally, U.S. Pat. Nos. 4,180,691, 3,870,765, 4,396,556, and 4,684,459 all disclose processes for the liquid acid alkylation of hydrocarbon in the presence of a surfactant. However, none of these patents discusses that such a process can occur in an alkylation reaction zone comprising a fixed bed of activated carbon.

DESCRIPTION OF THE DRAWING

The drawing represents a preferred embodiment of the flow scheme of the process of this invention. A first hydrocarbon feed comprising an olefin-acting agent such as a $C_2$-$C_{20}$ olefinic hydrocarbon is introduced into the reaction zone 6 through line 1. A second hydrocarbon feed stream comprising a hydrocarbon substrate such as an isoparaffin or benzene is introduced into the reaction zone 6 through line 13. The hydrocarbon substrate of line 13 consists of fresh hydrocarbon substrate from line 2 combined with recycle hydrocarbon substrate from line 4. The final feed component to the reactor zone 6 comprises a liquid acid alkylation catalyst comprising a liquid acid and a surfactant which is introduced into the reaction zone through line 14. The liquid acid catalyst of line 14 is comprised of a mixture of fresh liquid acid catalyst from line 3 mixed with recycle liquid acid catalyst from line 5.

The three feed components form an emulsion type admixture in the reaction zone 6. The admixture passes through a fixed bed of contact-material 7, within the reaction zone 6 with the contact material improving the contacting between the liquid acid catalyst and the two hydrocarbon feedstocks. After a reactor residence time of from 2.0 to 60.0 $hr^{-1}$, the admixture exits the reaction zone 6 through line 8.

The reaction zone effluent passes through line 8 into a separator vessel 9. In the separator vessel 9, the hydrocarbons are separated from the liquid acid alkylation catalyst. The liquid acid alkylation catalyst is recycled through line 5 to the reaction zone, while the hydrocarbon phase is directed through line 10 to the separation zone 11.

The separation zone 11 can be configured in any manner such that the desired product and recycle hydrocarbons are recovered in essentially pure form. The product hydrocarbon of the separation zone 11 are recovered through line 12 while the recycle hydrocarbon substrate is recycled to the reaction zone through line 4.

This drawing is a schematic outline of the basic method of this invention. It is not intended to place any limitation on the scope or practice of the invention or to exclude the large number of variations in this general flow scheme which are apparent to those skilled in the art. Various required subsystems such as pumps, valves, control systems, fractionators, and the like have been deleted for the purposes of simplicity and clarity of presentation.

DETAILED DESCRIPTION OF THE INVENTION

This invention relates to a process for alkylating a reaction mixture comprising an olefin acting agent and a hydrocarbon substrate with a liquid acid alkylation catalyst comprising a liquid acid such as sulfuric acid or hydrofluoric acid and a surfactant in an alkylation reaction zone containing a fixed bed of inert particulate contact material. Hydrocarbon substrates which may be alkylated in the process of the present invention include paraffinic and aromatic hydrocarbons. Typical paraffins include isobutane and higher homologues having a tertiary carbon atom, such as 2-methylbutane and 2,4-dimethylpentane. Other alkylatable materials include benzene, toluene, xylene, naphthenes, phenols, cresols, amines, thiophenes, and isoparaffinic mercaptans. It is preferred that the hydrocarbon substrate is either isobutane or benzene.

Olefin acting agents also comprise a feed component to the process of the instant invention. Suitable olefin acting agents are typically straight or branched hydrocarbons containing one or more carbon-carbon double bond. It is preferred that the olefin acting agent contain from 2 to 20 carbon atoms, and it is most preferred that the olefin acting agent contain from 3 to 5 carbon atoms.

The alkylation reaction is promoted through the presence of a liquid acid alkylation catalyst comprising a liquid acid such as hydrofluoric acid, sulfuric acid, phosphoric acid, and the like, or mixtures thereof along with a surfactant described below. These acid alkylation catalysts are maintained in a liquid phase containing a minimum of water to reduce corrosion problems. The liquid acid may also comprise a mixture of a mineral acid with a Friedel-Crafts metal halide such as aluminum chloride, aluminum bromide, boron trifluoride, and other proton donors.

Additionally, it is anticipated that the liquid acid alkylation catalyst of the instant invention may contain compounds such as surfactants, alcohols, MTBE, and the like liquid compounds known to assist in the promotion of acid catalyzed alkylation process. Furthermore, it is anticipated that the process of the present invention may be accomplished with any liquid acid alkylation catalyst known in the prior art. It is preferred however that the liquid acid alkylation catalyst comprise either sulfuric acid or hydrofluoric acid.

The second component of the liquid acid alkylation catalyst is the surfactant component. The preferred surfactant will be cationic or anionic in character. The cationic or anionic surfactant component is an integral part of the acid catalyst as it allows the process to be operated at reduced liquid acid catalyst rates while maintaining good product octane values. The tremendously large number of compounds which may be characterized as surfactants has prevented the development of a definitive characterization of this group of compounds. As used herein, the term "surfactant" is intended to indicate a compound which satisfies the six fundamental characteristics set out on page 507 of Volume 19 of *Kirk-Othmer Encyclopedia of Chemical Technology*, 2nd Edition, Interscience Publishers, 1969. These six fundamental characteristics include solubility in at least one phase of a liquid system, an amphipathic structure, the tendency to form oriented monolayers at phase interfaces, preferential equilibrium concentration at a phase interface as compared to the bulk of a solution, micelle formation, and the possession of some combination of the functional properties of surfactants, which include detergency, foaming, wetting, emulsifying, solubilizing, and dispersing.

Surfactants are classified as being cationic, anionic, or neutral depending on their solubilized charge. Preferably, the surfactant of the instant invention is a cationic or anionic surfactant. A cationic surfactant is one that exhibits a positive charge when solubilized. Conversely, an anionic surfactant is one that exhibits a negative charge when solubilized. Additionally, the preferred cationic or anionic surfactant is a hydrophilic material which is soluble in the acid catalyst phase of the two phase alkylation reaction system. It is believed that the cationic and anionic surfactants are most useful in the instant process because they optimally increase the solubility of the primary reactant isobutane in the acid phase of an acid-catalyzed alkylation process. The increase in the isobutane HF acid solubility created by the preferred surfactant allows HF acid concentration to be reduced in order to return the process to similar reaction mixture levels of isobutane in the HF acid.

It is preferred that the cationic or anionic surfactant utilized in the acid catalyst of the instant invention be comprised of a small, stable cationic surfactant. By "small", it is meant a cationic surfactant containing no aliphatic or aromatic groups having more than 10 carbon atoms, and preferably no more than 7 carbon atoms.

It is also preferred that the cationic or anionic surfactant component of the acid catalyst contain a sulfur or a phosphorus component. Cationic and anionic surfactants containing such components have been found to be very effective as a portion of the acid catalyst of the instant invention. In the case where a cationic surfactant is used as a portion of the acid catalyst of the instant invention, the preferred sulfur and phosphorus components in the cationic surfactant will take the form of sulfonium or phosphonium salts. These salts will have the general structure:

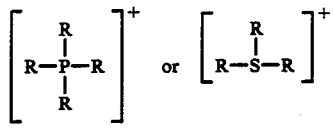

where R is an aliphatic or aromatic compound of 10 carbon atoms or less and preferably of 7 carbon atoms or less.

It is preferred that the small, stable cationic surfactant of the instant invention is tetrabutylphosphonium bromine.

As previously mentioned, the preferred anionic surfactant used as a portion of the novel acid catalyst in the instant alkylation process preferably contains a sulfur or phosphorus compound. Such components in an anionic surfactant will typically take the form of a sulfonic or phosphonic compound. Sulfur containing or sulfonic anionic surfactants may be present as: sulfates and sulfated compounds like sulfated esters, sulfated alkanolamides, alkyl sulfates and the like, or as sulfonates with the formula $R-SO_3^-$ where R may be an aliphatic compound, aromatic, alkylaromatic, naphthalene, an olefin, and other similar hydrocarbon compounds.

Phosphorus-containing or phosphonic anionic surfactants useful in the acid catalyst of the instant invention include alkylphosphates, alkylpolyphosphates, phosphate mono- and diesters of the formulae:

$R-(OCH_2CH_2)_4OPO_3H^-$ -monoester

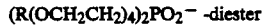
$(R(OCH_2CH_2)_4)_2PO_2^-$ -diester and the like phosphorus-containing anionic surfactants.

It is preferred that the hydrocarbon group components represented by the symbol R in the formulae above comprise aliphatic or aromatic compounds of no more than 10 carbon atoms and preferably no more than 7 carbon atoms. It is most preferred that the anionic surfactant of the instant invention is diisobutylthiophosphinate.

It is an aspect of the instant invention that the surfactant component of the instant catalyst may contain a mixture of both an anionic and cationic surfactant. Additionally, the cationic or anionic surfactant of the instant invention as previously noted should be soluble in the liquid acid portion of the acid catalyst and therefore becomes a constituent of the hydrofluoric acid-containing catalyst. The desired surfactant component is recoverable as a portion of the acid catalyst in the acid catalyst separation zone. However, in the catalyst regeneration zone, a small portion of the surfactant is separated from the HF acid by fractionation and typically removed from the process as a portion of a heavy by-product stream. However, as mentioned, this lost surfactant portion is typically only a very small portion of the total process inventory of surfactant and therefore the anticipated surfactant make-up requirements are expected to be small.

As heretofore indicated, an object of the present invention is the production of a high octane alkylate by means of an acid-catalyzed alkylation of an isoparaffin with an olefin-acting agent in an alkylation reactor having a fixed bed of activated carbon or the reduction of the liquid acid-to-olefin volumetric feed ratio to produce a product with an octane equivalent to a prior art process operating at a high acid rate. It is believed that utilizing a liquid acid alkylation catalyst comprising an anhydrous mixture of from about 50 to 99.9 volume percent of a liquid acid and from about 0.1 to 50.0 volume percent of a surfactant component is preferred. The liquid acid alkylation catalyst most preferably comprises from 90.0 to 99.9 volume percent of a liquid acid catalyst and from 0.1 to 10.0 volume percent of a surfactant.

Alkylation conditions in general include a pressure sufficient to maintain the hydrocarbons and acid in a liquid phase, with a general range being from about 1 to 40 atmospheres. The alkylation reaction may take place at temperatures of from 0°-390° C. with a range from 0°-275° C. being more preferred. The reaction also occurs at liquid hourly space velocities ranging from 0.1 to 100 $hr^{-1}$ and preferably at a space velocity of from 0.5 to 60 $hr^{-1}$.

Another important alkylation reaction process variable is the molar ratio of the hydrocarbon substrate to the olefin acting agent. As known to those skilled in the art, typical alkylation zone conditions necessarily include a high ratio of the molar concentration of the hydrocarbon substrate to the molar concentration of the olefin acting agent in order to produce a high quality alkylate product. A broad range of this ratio is from about 3 to about 20 with a preferred operating range being from 5 to 16.

A second and very important feed ratio of the process of the present invention is the molar ratio of the liquid acid alkylation catalyst to the olefin acting agent being fed to the alkylation reaction zone. The minimization of this ratio is an important aspect of the process of the instant invention. A low molar ratio of acid catalyst to olefin acting agent means less acid catalyst is required in the process. It also means that a smaller supply of acid is required to maintain acid inventory. By minimizing this ratio, the volume of acid catalyst necessary is minimized resulting in a reduction in the potential environmental and safety dangers posed by the acid catalyst. Thus, for this process, the acid to olefin molar feed ratio may vary from 0.01 to 100; however, a ratio in the range of 0.05 to 10 is most preferred for safety purposes.

It is preferred that the liquid acid catalyzed alkylation process of the instant invention be used to produce a high octane motor fuel product. To accomplish this, the feedstock to the process should comprise a $C_3$-$C_5$ olefinic hydrocarbon, an isoparaffin, and hydrofluoric acid. Optimum reaction zone conditions for the production of a motor fuel alkylate from these feed components includes a temperature of from 0° to 50° C., a pressure of from 1 to 20 atmospheres, a liquid hourly space velocity of from 2 to 60 $hr^{-1}$, and a hydrofluoric acid to $C_3$-$C_5$ olefin molar feed ratio of from 0.05 to 10. This feed ratio corresponds to an HF to $C_3$-$C_5$ olefin volumetric feed ratio of from about 0.1 to 16.7.

A general flow of an alkylation process designed for the production of high octane number motor fuel comprises the steps of contacting a mixture of the two hydrocarbons to be reacted with the liquid acid catalyst, mixing the reactants and the liquid catalyst in the reaction zone to form an emulsion, allowing the emulsion to soak for a length of time during which some agitation or turbulence is maintained to sustain the emulsion, passing the emulsion into a settling zone in which separate liquid acid catalyst, and hydrocarbon phases form, and withdrawing the separate liquid phases from the settling zone. It is common practice, at this point, to recirculate at least a portion of the liquid acid catalyst phase to the reaction zone. This recirculated liquid catalyst is often cooled so that it functions as a heat sink for the exothermic reaction. A large amount of unreacted isoparaffins or aromatics is present in the withdrawn hydrocarbon phase. This material may be recovered from the separated liquid hydrocarbon phase by such methods as flashing or fractionation and also recirculated to the reaction zone. Some processes do not utilize a soak zone at all and still others contact the separated hydrocarbon phase with a regenerated high strength acid stream to aid in acid removal.

The reaction vessel used to practice this invention can be any type of vessel constructed to withstand the pressure, temperature, and corrosive conditions of an acid catalyzed alkylation operation, but is preferably a cylindrical steel vessel being relatively elongated and vertically positioned. The top and bottom walls of the receiving vessel can be flat plates or can be spherically shaped caps. For purposes of description, the receiving vessel may be divided into upper and lower sections, generally equal to the upper and lower half respectively of the vessel. Preferably, however, the upper section comprises the upper quarter of the vessel while the lower section comprises the lower quarter of the vessel. The feed inlet means are preferably vertically positioned tubes which are located in the upper or lower section of the receiving vessel so that their respective outlets discharge a nondispersed high velocity stream of unreacted hydrocarbons in an upward or downward direction. The fluid standpipe can be one or more small diameter vertical pipes which pass through the receiving vessel and which may be connected to a manifold arrangement used for distribution of the hydrocarbon through the standpipes. The standpipe may have a nozzle located on its outlet, and more than one standpipe may be utilized.

It is an important aspect of the process of the present invention that the reaction zone contain a fixed bed of inert particulate contact material. The fixed bed of particulate contact material should be uniform in depth and cover the entire cross-section of the reactor vessel. The fixed bed of inert contact material should fill from 10% to 100% of the reactor volume. The inert particulate contact material may be in the form of tablets, extrudates, spheres, or randomly shaped naturally occurring pieces. An 8×20 mesh material is especially suitable. Natural materials such as clays and silicates or refractory inorganic oxides may be used as the inert contact material. The material may therefore be formed from diatomaceous earth, kieselguhr, kaolin, alumina, zirconia, etc. It is especially preferred that the catalyst comprises a carbon-containing support, particularly charcoals which have been thermally and/or chemically treated to yield a highly porous structure similar to activated carbon, and especially activated carbon itself.

The bed of particulate contact material is very useful in the process of the present invention. The inert bed of contact material improves the efficiency of the alkylation reaction resulting in increased desired product yield at constant reaction conditions. The efficiency improvement gained from the use of the bed of inert contact material allows the process to be operated at a lower acid to olefin feed ratio while maintaining standard product quality.

It is believed that the fixed bed of inert contact material improves the efficiency of the alkylation reaction by assisting in the maintaining of the hydrocarbon, liquid acid emulsion. Further, the inert bed of contact material provides an extended surface upon which the two immiscible liquids may react. It is believed that particulate contact materials with high surface areas are most useful in the instant process.

In the description of the preferred embodiments herein provided, it is intended that both the alkylation reactor and a reaction soaker, if one is utilized, are included within the scope of the term "alkylation reaction zone". Suitable reaction soakers are well known in the art. For example, the reaction soakers described in U.S. Pat. Nos. 3,560,587 and 3,607,970 may suitably be employed in the present process. Such reaction soakers are conventionally vessels equipped with perforated trays, baffle sections, or the like to maintain an alkylation reaction mixture in the form of a fairly homogeneous mixture, or emulsion, for a predetermined length of time. The alkylation reaction mixture of catalyst and hydrocarbons is maintained in the reaction soaker for a time which depends on the composition of the reaction mixture. Generally, a reaction soaker residence time of about 1 minute to about 30 minutes is employed. The temperature and pressure maintained in the reaction soaker are substantially the same as the temperature and pressure maintained in the associated alkylation reactor.

Means for settling the reaction mixture effluent from the alkylation reaction zone in order to separate a settled hydrocarbon phase and the liquid acid catalyst phase are well known in the alkylation art. Generally, the effluent alkylation reactor mixture recovered from an alkylation reactor or soaker comprises a mixture of unreacted hydrocarbons, alkylation reaction products, acid catalyst, and catalyst-soluble organic materials, possibly with small amounts of light hydrocarbons, etc. When this alkylation reaction mixture is allowed to stand unstirred, i.e., settled, the alkylation reaction products, hydrocarbon substrate, and light hydrocarbons form a lighter settled hydrocarbon phase. The liquid acid catalyst phase comprising the liquid acid and surfactant forms a separate phase. The settled hydrocarbon phase is then simply mechanically separated from the catalyst phase. The temperature and pressure maintained during such a settling operation are substantially the same as those described above in connection with the alkylation conditions employed in the reaction zone. The hydrocarbons and the catalyst are preferably in the liquid phase during the settling separation operation.

Some means for withdrawing heat from alkylation zone may be necessary for optimum operation of the process. A variety of means for accomplishing the heat withdrawal are well known. For example, the heat generated in the alkylation reaction may be withdrawn from the alkylation reactor by indirect heat exchange between cooling water and the reaction mixture in the reactor.

It is also an aspect of the alkylation process of the instant invention that the hydrocarbon phase recovered from the separator be further fractionated to purify product and feed hydrocarbons for recovery or recycle purposes. It is also an aspect of the process of the instant invention that the liquid acid alkylation catalyst recovered from the separator be recycled back to the alkylation reaction zone directly, or be purified or regenerated by means known in the art before being recycled to the alkylation reaction zone.

In order to demonstrate the benefits and advantages of the present invention in contrast to prior art alkylation methods, the following example is offered. It is to be understood that this example is intended to be illustrative and in no way restrictive on the otherwise broad embodiments of the present invention as set forth in the claims appended hereto.

EXAMPLE I

A more complete understanding of the process may be facilitated by the following description of an alkylation process employing the novel aspects of this invention. Isobutane is charged to the alkylation process at a rate of about 720 barrels per hours. Mixed propylene and butylenes are admitted to the process at a rate of about 60 barrels per hour, and said olefins are admixed with the isobutane reactant. The hydrocarbon reactant stream is continued through multiple lines into an alkylation reactor. The liquid acid alkylation catalyst comprising from 90.0 to 99.9 volume percent of substantially anhydrous hydrofluoric acid and from 0.1 to 10.0 volume percent of the surfactant diisobutylthiophosphinate or tetrabutylphosphonium bromide is charged to the reactor at a rate of about 200 barrels per hour. Alkylation conditions maintained in the alkylation reactor include a temperature of from about $-1°$ to about $43°$ C., and a pressure of from about 14 to about 20 atmospheres. The reaction mixture is processed through the alkylation reactor at a rate to allow an average residence time therein of from about 0.2 to about 2 minutes. In addition, the alkylation reaction zone is almost entirely packed (100% of void volume) with activated carbon. The alkylation reactor effluent is recovered and transferred to an upper settling chamber of an elongated, unitary vessel. In the upper settling chamber, the liquid acid alkylation catalyst is allowed to settle and gravitate downwardly to form a lower acid catalyst phase and an upper hydrocarbon phase therein. The acid phase is allowed to gravitate downwardly from said upper settling chamber at a rate of 200 barrels per hour to be discharged into a lower portion of a middle settling chamber. The upper hydrocarbon phase which accumulates in the upper settling chamber is withdrawn at the rate of about 752 barrels per hour and transferred directly to a lower soaking chamber. The hydrocarbon phase is charged to said lower soaking chamber in admixture with hydrofluoric acid recovered from the aforementioned middle settling chamber and passed through an acid recycle conduit at the rate of 75.2 barrels per hour as hereinafter related. The acid-hydrocarbon mixture is processed upwardly through said lower soaking chamber at a rate to provide an average residence time therein of about 10 minutes. Soaking conditions further include a temperature of from about $-1°$ to about $43°$ C. and a pressure of from about 14 to about 20 atmospheres. The lower soaking chamber is designed to provide a pressure drop of from about $-10$ to about 2 atmospheres. The acid-hydrocarbon mixture is recovered from a lower soaking chamber through an overhead chimney and discharged into the middle settling chamber wherein the mixture is allowed to settle and effect a substantially complete separation of the acid and hydrocarbon components. The acid-hydrocarbon mixture discharged from the lower soaking chamber into the middle settling chamber will thus provide an upper hydrocarbon layer in said middle settling chamber and a portion of the lower acid phase contained therein. The upper hydrocarbon phase is withdrawn from said middle settling chamber, and from said unitary soaking-settling vessel at the rate of 752 barrels per hour. Said hydrocarbon phase is further processed for the recovery of alkylate product, and for the recovery and recycle of unreacted isobutane, by conventional means, not shown.

The lower acid phase is recovered from the middle settling chamber at a rate of about 213 barrels per hour. About 13.0 barrels of acid per hour are diverted from said acid transfer conduit through an acid recycle conduit and passed through a circulating pump to be admixed with the aforementioned hydrocarbon phase transferred to the lower soaking chamber. The balance of the lower acid phase from said middle settling chamber, about 200 barrels per hour, is recycled to the alkylation reactor.

EXAMPLE II

This example was conducted in a pilot plant scale unit operation. The pilot plant comprised a monel autoclave in which an isoparaffin and olefin-acting agent are contacted with a once-through stream of hydrofluoric acid catalyst. After sufficient time, the hydrocarbon and acid phases are removed from the autoclave and passed to a settler in which the phases are allowed to separate. The hydrocarbon phase comprising alkylate is removed from the settler and passed to neutralization facilities. Thereafter, the hydrocarbon phase is collected for analysis.

In this example, five different runs were made in the pilot plant. The first two runs were at different acid to olefin molar feed ratios and used a reactor with no packing. The third and fourth runs employed a reactor with 10 and 30 volume percent of activated carbon packing at an acid to olefin molar feed ratio of 7. The fifth test utilized 30 volume percent of activated carbon packing and an alkylation catalyst containing 5.0 wt.% MTBE (methyltertiarybutylether).

In all four runs, the processing conditions were identical, and comprised a temperature of $20°$ C., a pressure of 8.8 atmospheres, a residence time of 10 minutes, and a stirring rate of 1800 rpm. The volumetric ratio of the acid phase feed rate to the olefin feed rate was held at 57 to the first run and at 7.0 for all other runs. The mole ratio of isobutane to $C_4$ olefins was 7.5. The $C_4$ olefin molar distribution was 46.9% 2-butene, 34.8% 1-butene, and 28.3% isobutylene.

In each run, the alkylate product was analyzed and the products were found to have the compositions and research octane numbers as set forth in Table 1 below.

TABLE 1

| Conditions | Feedstock | | | | |
|---|---|---|---|---|---|
| Temp. - 20° C. | i-$C_4$/$C_4^=$ (mole/mole) = 7.5 | | | | |
| Pressure - 8.85 atm | $C_4^=$ —2/$C_4^=$ —1/i$C_4^=$ = 46.9/34.8/28.3 | | | | |
| Stirring Rate - | (mol. %) | | | | |
| 1800 rpm | HF/$C_4^=$ (mole/mole) : 7 | | | | |
| Catalyst: | HF | HF | HF | HF | 95% HF 5% MTBE |
| HF/$C_4^=$ (mole/mole) | 57 | 7 | 7 | 7 | 7 |
| Packing, Vol. % | None | None | 10% | 30% | 30% |
| Alkylate Yield, % | 99.1 | 99.4 | 99.7 | 99.5 | 99.6 |
| Alkylate Composition, Wt. %: | | | | | |
| $C_8^-$ | 7.9 | 7.5 | 7.5 | 7.9 | 8.2 |
| TMP | 70.2 | 66.2 | 66.8 | 68.8 | 69.6 |
| DMH | 16.0 | 20.7 | 20.1 | 18.0 | 16.1 |
| $C_8^+$ | 5.9 | 5.6 | 5.6 | 5.3 | 6.1 |
| RON | 93.2 | 90.8 | 91.0 | 91.9 | 92.7 |

The results set forth in the Table indicate that product octane (RON) increases with increasing volumes of reactor packing. The addition of an MTBE component results in an even greater octane improvement. The octane improvement is explained by comparing the amount of TMP (trimethylpentane) to DMH (dimethylhexane) produced in each run. TMP has an octane value of 103 while DMH has an octane value of 70 on average. Thus, the conditions which produce larger amounts of TMP in comparison to DMH will typically result in a product with a higher octane value.

The first run mimics an alkylation process utilizing a typical HF/$C_4^=$(mole/mole) feed ratio of 57. The octane of a product produced by the feedstock is 93.2. When the HF/$C_4^=$(mole/mole) feed ratio is dropped to 7, the product octane also falls to 90.8. Adding packing to the reactor at the low feed acid to olefin feed ratio results in an octane of 91.0 at 10% reactor packing volume, and a 91.9 octane at a 30% reactor packing volume. Pilot plant constraints prevented the evaluation of larger packing volumes at the lower acid to olefin molar feed rate, but the trend indicates that the product octane rises with increased reactor packing volumes. The example therefore shows that a product octane essentially equivalent to that produced at high acid to olefin feed ratios is obtainable at low acid to olefin feed rates by utilizing a reactor packing comprising a particulate contact material.

What is claimed is:

1. A process for the liquid phase alkylation of an olefin acting agent with a hydrocarbon substrate in the presence of a liquid acid alkylation catalyst comprising a surfactant and a liquid acid which comprises the steps of:
   (a) introducing reactants comprising an olefin acting agent, a hydrocarbon substrate, and a liquid acid alkylation catalyst into an alkylation reaction zone operating at alkylation reaction conditions and containing a fixed bed of activated carbon to create a reaction mixture;
   (b) passing the reaction mixture through the fixed bed of activated carbon in the alkylation reaction zone and into a separator;
   (c) separating the liquid acid alkylation catalyst from the product and unreacted feed hydrocarbons;
   (d) withdrawing the hydrocarbons from the separator and purifying and recovering the product hydrocarbons and the unreacted hydrocarbons of the liquid phase alkylation reaction; and
   (e) recycling at least a portion of the separated acid alkylation catalyst back to the alkylation reactor inlet.

2. The process of claim 1 further characterized in that the liquid acid of the liquid acid alkylation catalyst comprises sulfuric acid.

3. The process of claim 1 further characterized in that the liquid acid of the liquid acid alkylation catalyst comprises hydrofluoric acid.

4. The process of claim 3 further characterized in that the liquid acid catalyst comprises from 0.10 to 50.0 volume percent of a surfactant and from 50 to 99.9 volume percent of hydrofluoric acid.

5. The process of claim 4 further characterized in that the olefin acting agent comprises a $C_2$-$C_{20}$ olefinic hydrocarbon.

6. A process for the liquid phase alkylation of a $C_2$-$C_{20}$ olefinic hydrocarbon with a hydrocarbon substrate in the presence of a liquid acid catalyst comprising from 0.10 to 50 volume percent of a surfactant and from 50 to 99.9 volume percent of hydrofluoric acid, the process comprising the steps of:
   (a) introducing reactants comprising $C_2$-$C_{20}$ olefinic hydrocarbons, a hydrocarbon substrate and the liquid acid catalyst into an alkylation reaction zone to create a reaction mixture where the alkylation reaction zone is at alkylation reaction conditions including a temperature of from 0°–275° C., a pressure of from 1 to 40 atmospheres, a liquid acid catalyst to olefinic hydrocarbon molar feed ratio of from 0.1 to 100, and a reactor space velocity of from 0.5 to 60 $hr^{-1}$, and where the alkylation reaction zone contains a fixed bed of activated carbon;
   (b) passing the reaction mixture through the fixed bed of activated carbon in the alkylation reaction zone, and into a separator;
   (c) separating the liquid acid catalyst from the hydrocarbon product and unreacted feed hydrocarbons;
   (d) withdrawing the hydrocarbons from the separator and purifying and recovering the product hydrocarbons and the unreacted hydrocarbons of the liquid phase alkylation reaction; and
   (e) recycling at least a portion of the separated hydrofluoric acid to the inlet of the alkylation reactor.

7. The process of claim 6 further characterized in that the hydrocarbon substrate comprises benzene.

8. The process of claim 6 further characterized in that the hydrocarbon substrate comprises an isoparaffin.

9. The process of claim 8 further characterized in that the $C_2$-$C_{20}$ olefinic hydrocarbons comprise $C_3$-$C_5$ olefins.

10. The process of claim 9 further characterized in that the fixed bed of activated carbon occupies from 10% to 100% of the reactor void volume.

11. A process for the liquid phase alkylation of a $C_3$-$C_5$ olefinic hydrocarbon with an isoparaffin in the presence of liquid acid catalyst which comprises from 0.1 to 10.0 volume percent of a cationic or anionic surfactant and from 90.0 to 99.9 volume percent of hydrofluoric acid, the process comprising the steps of:
   (a) introducing reactants comprising $C_3$-$C_5$ olefins, isoparaffins, and the liquid acid catalyst into an alkylation reaction zone containing 10–100% by volume of a fixed bed of activated carbon to create a reaction mixture where the alkylation reaction zone is at alkylation reaction conditions including a temperature of from 0° to 50° C., a pressure of from 1 to 20 atmospheres, a hydrofluoric acid to $C_3$-$C_5$ olefin molar feed ratio of from 0.05 to 10.0, and a reactor space velocity of from 2.0 to 60.0 $hr^{-1}$;

(b) passing the reaction mixture through the fixed bed of activated carbon in the alkylation reaction zone and out of the reaction zone and into a separator;

(c) separating the liquid acid catalyst from the product and unreacted feed hydrocarbons of the reaction mixture;

(d) withdrawing the hydrocarbons from the separator and purifying and recovering the product hydrocarbon and unreacted hydrocarbon of the liquid phase alkylation reaction; and (e) recycling at least a portion of the separated hydrofluoric acid to the inlet of the alkylation reactor.

12. The process of claim 11 further characterized in that the cationic or anionic surfactant component is soluble in the HF acid.

13. The process of claim 12 further characterized in that the cationic or anionic surfactant contains a sulfur or phosphorus component.

14. The process of claim 12 further characterized in that the cationic or anionic surfactant component is comprised of $C_{10}$ or smaller aliphatic or aromatic components.

15. The process of claim 12 further characterized in that the cationic or anionic surfactant component contains no aliphatic or aromatic groups having more than seven carbon atoms.

16. The process of claim 15 further characterized in that the anionic surfactant component is diisobutylthiophosphinate.

17. The process of claim 15 further characterized in that the cationic surfactant component is tetrabutylphosphonium bromide.

* * * * *